(12) United States Patent
Newell et al.

(10) Patent No.: US 9,398,847 B2
(45) Date of Patent: Jul. 26, 2016

(54) DEVICE FOR MEASURING INTERPUPILLARY DISTANCE IN A HEAD-MOUNTED DISPLAY UNIT

(71) Applicant: Valve Corporation, Bellevue, WA (US)

(72) Inventors: Dan Newell, Bellevue, WA (US); Benjamin David Krasnow, Redwood City, WA (US)

(73) Assignee: VALVE CORPORATION, Bellevue, WA (US)

( * ) Notice: Subject to any disclaimer, the term of this patent is extended or adjusted under 35 U.S.C. 154(b) by 222 days.

(21) Appl. No.: 14/058,241

(22) Filed: Oct. 19, 2013

(65) Prior Publication Data

US 2015/0109576 A1 Apr. 23, 2015

(51) Int. Cl.
| | |
|---|---|
| *A61B 3/10* | (2006.01) |
| *A61B 3/14* | (2006.01) |
| *A61B 3/11* | (2006.01) |
| *A61B 3/00* | (2006.01) |
| *A61B 3/024* | (2006.01) |
| *G02B 7/12* | (2006.01) |
| *G02B 27/01* | (2006.01) |
| *G02B 27/00* | (2006.01) |

(52) U.S. Cl.
CPC .............. *A61B 3/111* (2013.01); *A61B 3/0091* (2013.01); *A61B 3/024* (2013.01); *G02B 7/12* (2013.01); *G02B 27/0093* (2013.01); *G02B 27/017* (2013.01); *G02B 2027/014* (2013.01); *G02B 2027/0112* (2013.01); *G02B 2027/0134* (2013.01); *G02B 2027/0154* (2013.01)

(58) Field of Classification Search
USPC .......... 351/200, 203, 204, 205, 206, 209, 210, 351/211, 218, 222, 221, 223, 224, 228, 229, 351/230, 233, 235, 237, 246, 243
See application file for complete search history.

(56) References Cited

U.S. PATENT DOCUMENTS

| | | | | |
|---|---|---|---|---|
| 5,539,422 A * | 7/1996 | Heacock | ............ | G02B 27/0172 345/8 |
| 2012/0250152 A1* | 10/2012 | Larson | ............... | G02B 27/2264 359/464 |

* cited by examiner

*Primary Examiner* — Joseph P Martinez
*Assistant Examiner* — Brandi Thomas
(74) *Attorney, Agent, or Firm* — Barceló, Harrison & Walker, LLP

(57) ABSTRACT

In certain embodiments, a head-mounted display may include one or more displays for displaying images. A left and right movable disk may be placed respectively between the left and right eyes of a user and the one or more displays. The user may wear the HMD, and may adjust the spacing between the left and right disks while viewing the computer-displayed image or images through holes in the plastic discs. For example, the HMD may display a stereo colored bulls eye pattern, of which the user can only see a portion because their vision is restricted to on-axis viewing by the discs. The computer may instruct the user to move the HMD disks until the user can only see the color in the center of the bulls eye. In certain embodiments, by performing the foregoing adjustment, the eye may be oriented on the proper optical axis to look through an optimal location of a lens.

8 Claims, 9 Drawing Sheets

DEVICE FOR MEASURING INTERPUPILLARY DISTANCE IN A HEAD-MOUNTED DISPLAY UNIT

BACKGROUND OF THE DISCLOSURE

1. Field of the Disclosure

The disclosure relates generally to methods and systems of measuring interpupillary distance and positioning of a user's eyes with respect to one or more screen in a head-mounted display.

2. General Background

Head-mounted electronic displays have existed for many years. For example, helmet mounted displays were first deployed by the U.S. Army in the Apache helicopter in 1984. These head-mounted displays have many advantages over fixed displays. For example, head mounted displays may be relatively small and compact but can display images that, if they were to be displayed on conventional fixed displays, would require extremely large screens.

Head-mount display (MHD) units used for Virtual Reality (VR) applications have existed for decades, but the technology has never become mainstream. One factor that limits the utility of VR head-mount units is the difficulty in accurately setting the spacing between left and right displays to match the user's interpupillary distance. A mismatch may cause eyestrain and poor 3D perception.

Some existing HMDs allow the user to manually adjust the spacing between left and right displays, but the accuracy of the adjustment is often poor since users must move the displays until the image "looks correct." Without any feedback, the user must rely on their visual perception, which is often deceiving. This invention provides a reliable way to set the HMD lens positions that does not depend on subjective judgments.

There is a need in the art for a system that can quickly compensate for the user's head movement.

BRIEF DESCRIPTION OF THE DRAWINGS

By way of example, reference will now be made to the accompanying drawings, which are not to scale.

DETAILED DESCRIPTION

Those of ordinary skill in the art will realize that the following description of certain embodiments is illustrative only and not in any way limiting. Other embodiments will readily suggest themselves to such skilled persons, having the benefit of this disclosure. Reference will now be made in detail to specific implementations as illustrated in the accompanying drawings. The same reference numbers will be used throughout the drawings and the following description to refer to the same or like parts.

In general, a head-mounted display (HMD) may consist of an image projector mounted to the head that projects one or more images onto a screen in front of one or both of the user's eyes. Both the screen and the projector may be mounted onto the user's head such that they are in a fixed position relative to the user's eyes. The screen may be positioned between the projector and the user's eye in a rear-projection format or the screen may be positioned in front of both the projector and the eye in a front-projection format. Images on the display may be drawn as a series of discrete frames that may be displayed sequentially at high rate of speed. The frames may be displayed so rapidly that the human eye cannot detect individual frames but rather sees the series of images as continuous motion. The frames themselves may be drawn a line at a time and may take several microseconds to complete.

In certain embodiments, a head-mounted display may include one or more displays for displaying images. A left and right movable disk may be placed respectively between the left and right eyes of a user and the one or more displays. The user may wear the HMD, and may adjust the spacing between the left and right disks while viewing the computer-displayed image or images through the holes in the plastic discs. For example, the HMD may display a stereo colored bulls eye pattern, of which the user can only see a portion because their vision is restricted to on-axis viewing by the discs. The computer may instruct the user to move the HMD disks until they can only see the color in the center of the bulls eye. At this point, the computer may record the spacing between the lenses, which coincides with the interpupillary distance (IPD). Methods to measure the spacing include without limitation, a linear potentiometer, a rotary potentiometer with a connecting rod, a hall-effect sensor with one or more magnets, a linear variable differential transformer, an optical sensor with a code-strip, and an elastomeric potentiometer simple linear potentiometer. Once the user's IPD is known, the user can then remove the discs, and use the device normally. Alternately, the IPD adjustment could be done with the user reading a scale on the HMD and entering a number or other automatic computer monitored methods known to those of ordinary skill in the art.

Figure 1:
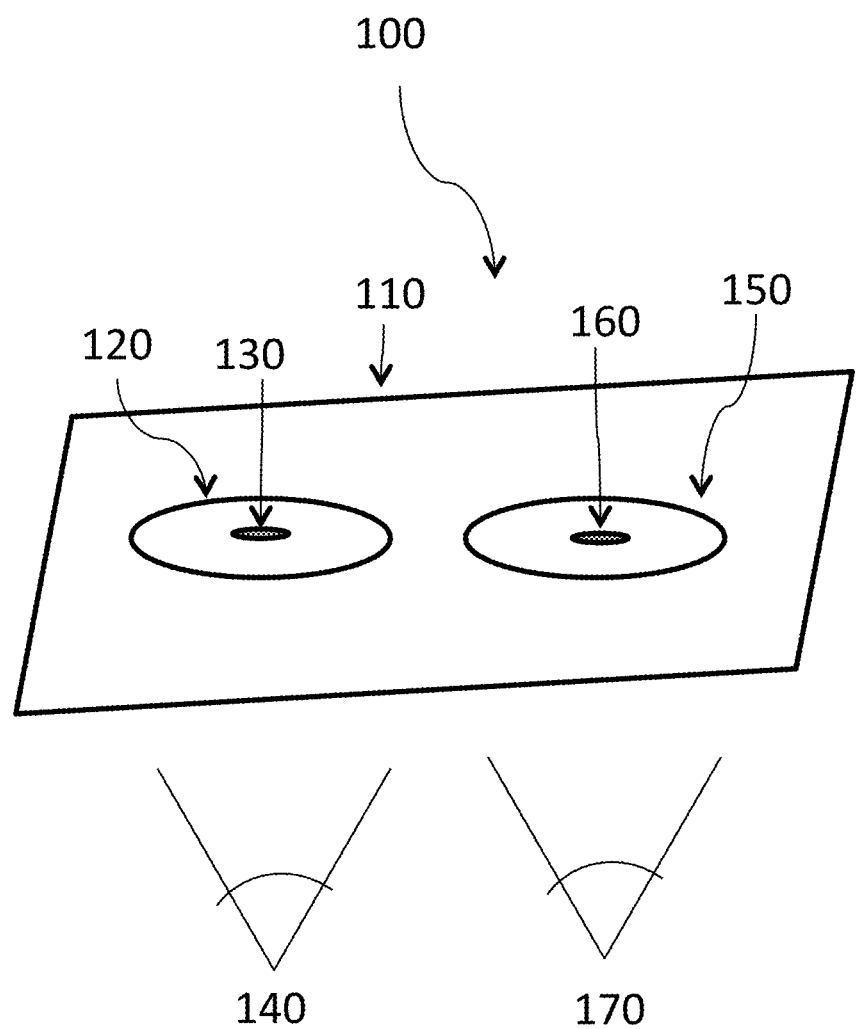
FIG. 1 illustrates a head-mounted display and its relevant components according to certain embodiments.

In certain embodiments as shown in FIG. 1, a head mounted display 100 may comprise one or more displays 110. A first movable disk 120 with a first hole 130 may be placed between a left eye of a user 140 and display 110. A second movable disk 150 with a second hole 160 may be placed between a right eye of a user 170 and display 110. In certain embodiments, a head-mounted display may include discs that may be temporarily fitted onto the one or more HMD display lenses by a user. In certain embodiments, the discs may each have a single hole in the center that forces vision through the hole to be on-axis with respect to the lens.

Figure 2:
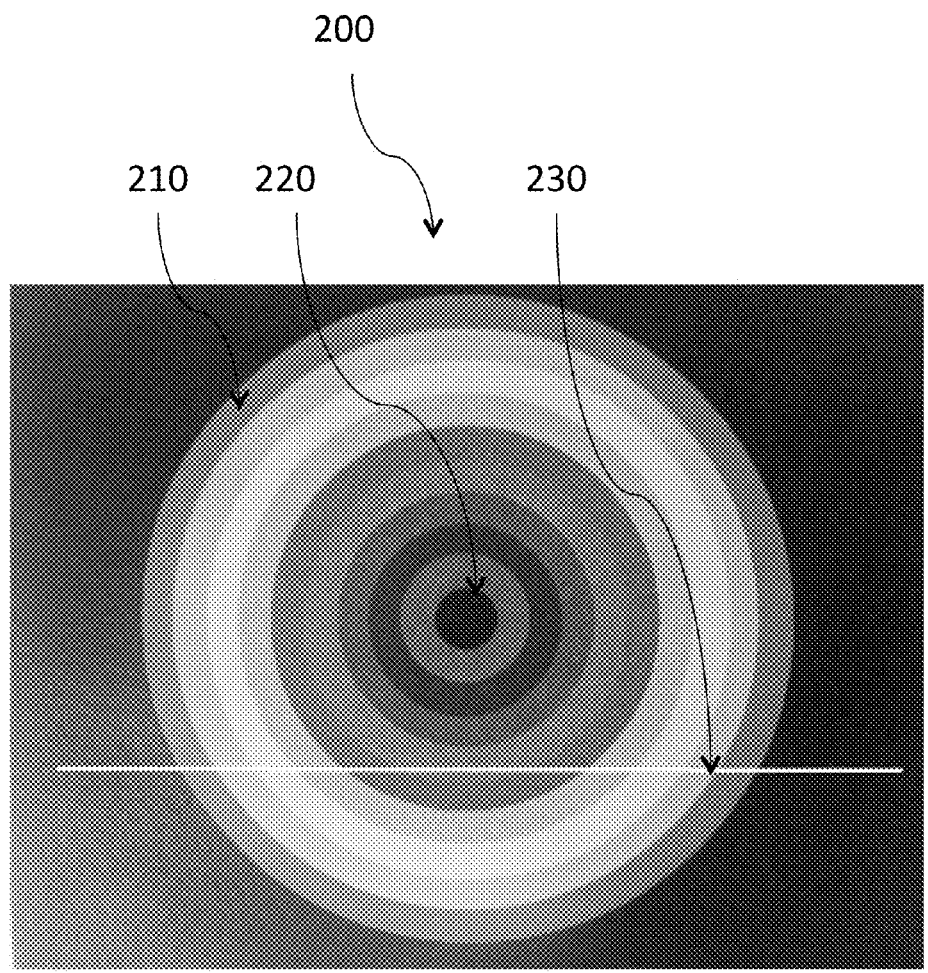
FIG. 2 illustrates a pattern for projecting on a head mounted display according to certain embodiments.

The user may wear the HMD, and may adjust the spacing between the left and right disks while viewing the computer-displayed image or images through the holes in the plastic discs. For example, the HMD may display a stereo colored bulls eye pattern 200, wherein a pair of bulls eyes comprising concentric colored bands 210 as shown in FIG. 2 are presented on display 110. The user may only be able to see a portion of each bulls eye because their vision is restricted to on-axis viewing by the discs. The computer may instruct the user to move the HMD disks until they can only see the color in the center of the bulls eye 220. At this point, the computer may record the spacing between the disks, which coincides with the interpupillary distance (IPD). Methods to measure the spacing include without limitation a linear potentiometer, a rotary potentiometer with a connecting rod, a hall-effect sensor with one or more magnets, a linear variable differential transformer, an optical sensor with a code-strip, and an elastomeric potentiometer simple linear potentiometer. Once the user's IPD is known, the user can then remove the discs, and use the device normally.

Calculating IPD may be very useful and may help to get the lenses into one axis of position, but this doesn't guarantee that the eye is still adequately centered. There may be additional information that may be ascertained during the process.

When attempting to measure the IPD, a user may have the HMD too high or too low so that the line between the eye and the first and second holes may never actually "hit" the bulls eye as the IPD adjustment is made. Line 230 in FIG. 2 shows one possible line of sight if the first disk is too low. If the user moves the first disk left and right along line 230 in an attempt to align the first hole over the center 220 of the bulls eye, the color viewed in through the hole will change, but will never match the color of the center 220 of the bulls eye. In order to guide the user to the center of the bulls eye, a succession of adjustments may be made to adjust the line of sight of each eye to the center of the respective bulls eyes in the stereo colored bulls eye pattern. It may be desirable first to adjust the HMD to the proper height relative to the eyes and then to adjust the HMD to the proper lateral position relative to the eyes. One of ordinary skill in the art will understand that a user can first adjust the HMD to the proper lateral position and then adjust to the proper height.

Figure 3:
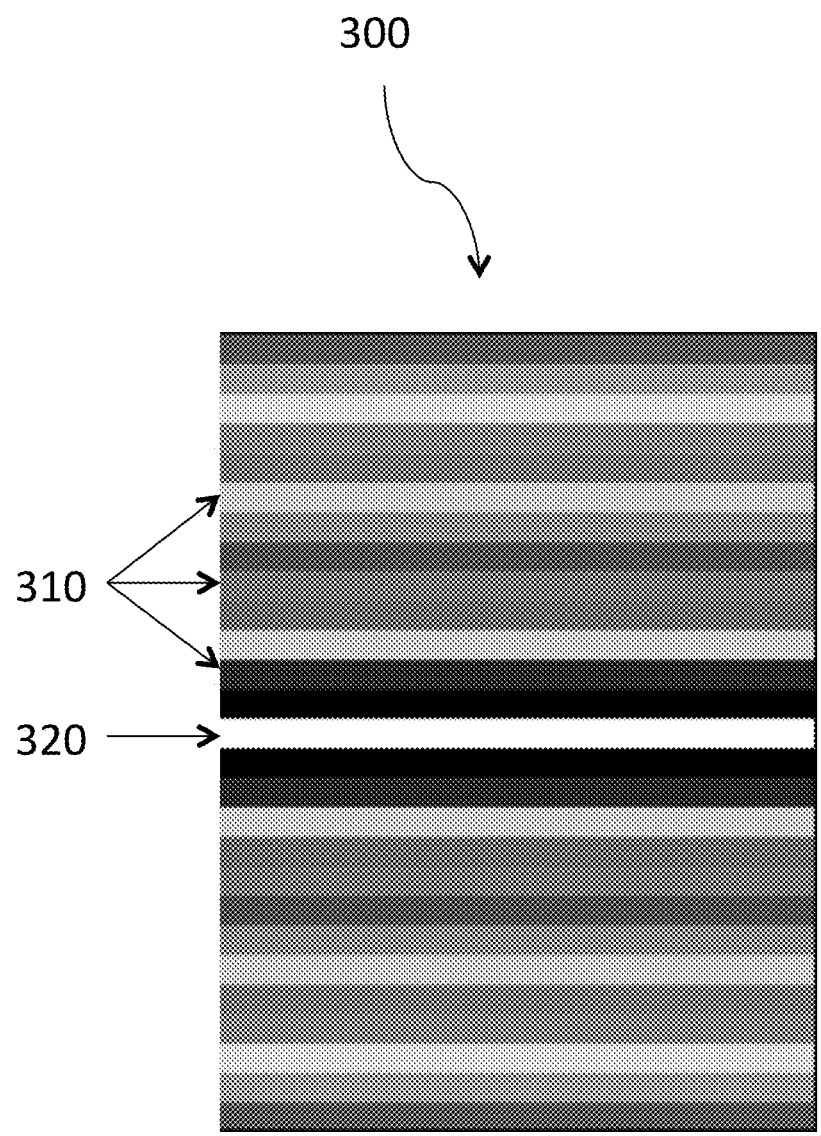
FIG. 3 illustrates a pattern for projecting on a head mounted display according to certain embodiments.

In certain embodiments as shown in FIG. 3, a pattern of horizontal colored stripes 300 may first be displayed on display 110 to provide a set a visual reference for whether the first hole 130 and/or the second hole 160 are located above or below the desired vertical position on display 110. The plurality of colored vertical stripes 310 may provide an indication to the user whether to move the first disk 120 and/or second disk 150 up or down on display 110 to align first hole 130 and second hole 160 with the central colored stripe 320.

Figure 4:
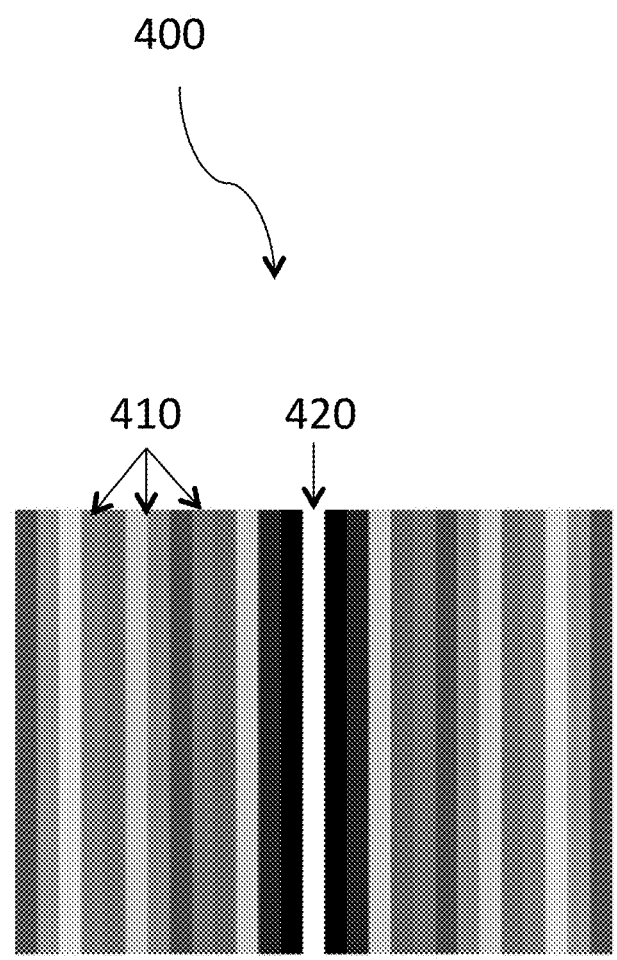
FIG. 4 illustrates a pattern for projecting on a head mounted display according to certain embodiments.

In certain embodiments as shown in FIG. 4, a pattern of vertical colored stripes 400 may first be displayed on display 110 to provide a set a visual reference for whether the first hole 130 and/or the second hole 160 are located left or right of the desired vertical position on display 110. The plurality of colored vertical stripes 410 may provide an indication to the user whether to move the first disk 120 and/or second disk 150 left or right on display 110 to align first hole 130 and second hole 160 with the central colored stripe 420.

The pattern of horizontal colored stripes 300 may be displayed before or after the pattern of vertical colored stripes 400, so that the vertical adjustment of the disks may be before either before or after the horizontal adjustment of the disks. In either case, a stereo color bulls eye may be displayed and the first disk 120 and/or second disk 150 may be moved relative to display 110 to align first hole 130 and second hole 160 with the center 220 of the respective bulls eyes of the stereo color bulls eye pattern to confirm that both axes of the eyes 140 and 170 are centered.

Figure 5:
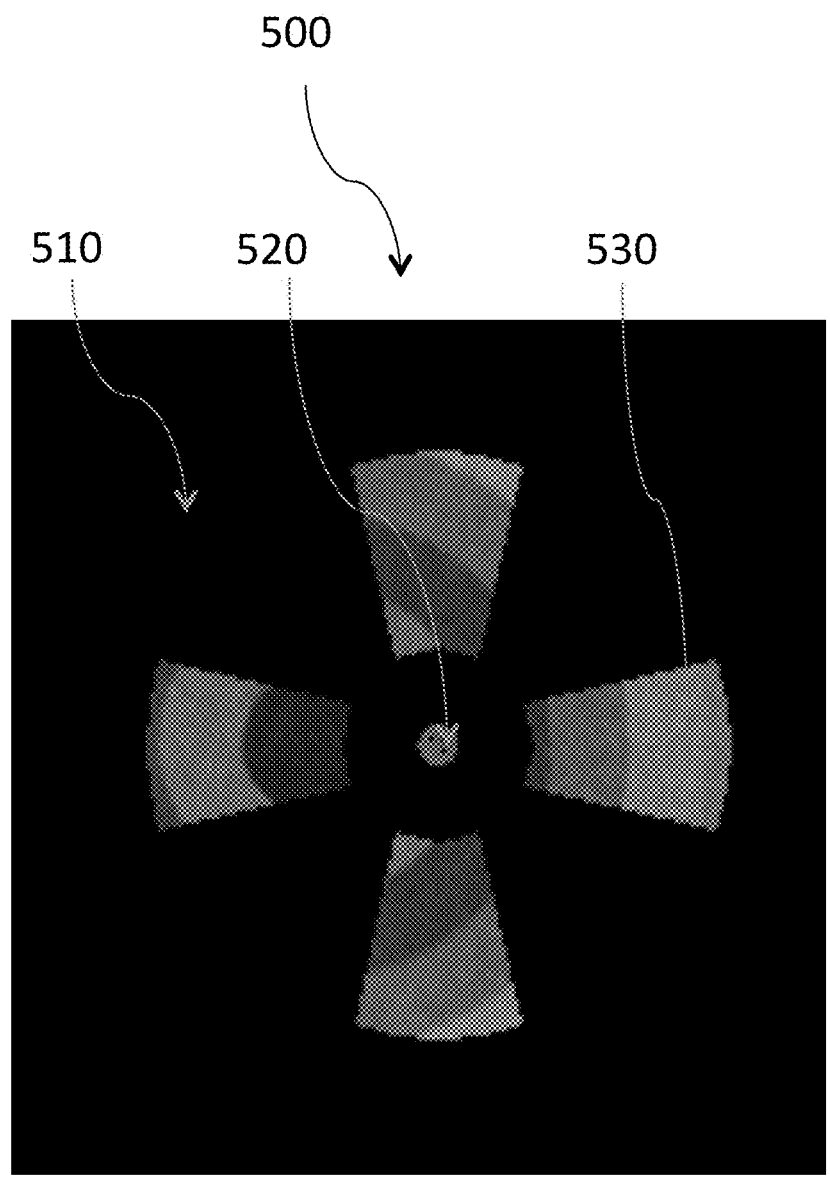
FIG. 5 illustrates a head-mounted display and its relevant components according to certain embodiments.
Figure 6:
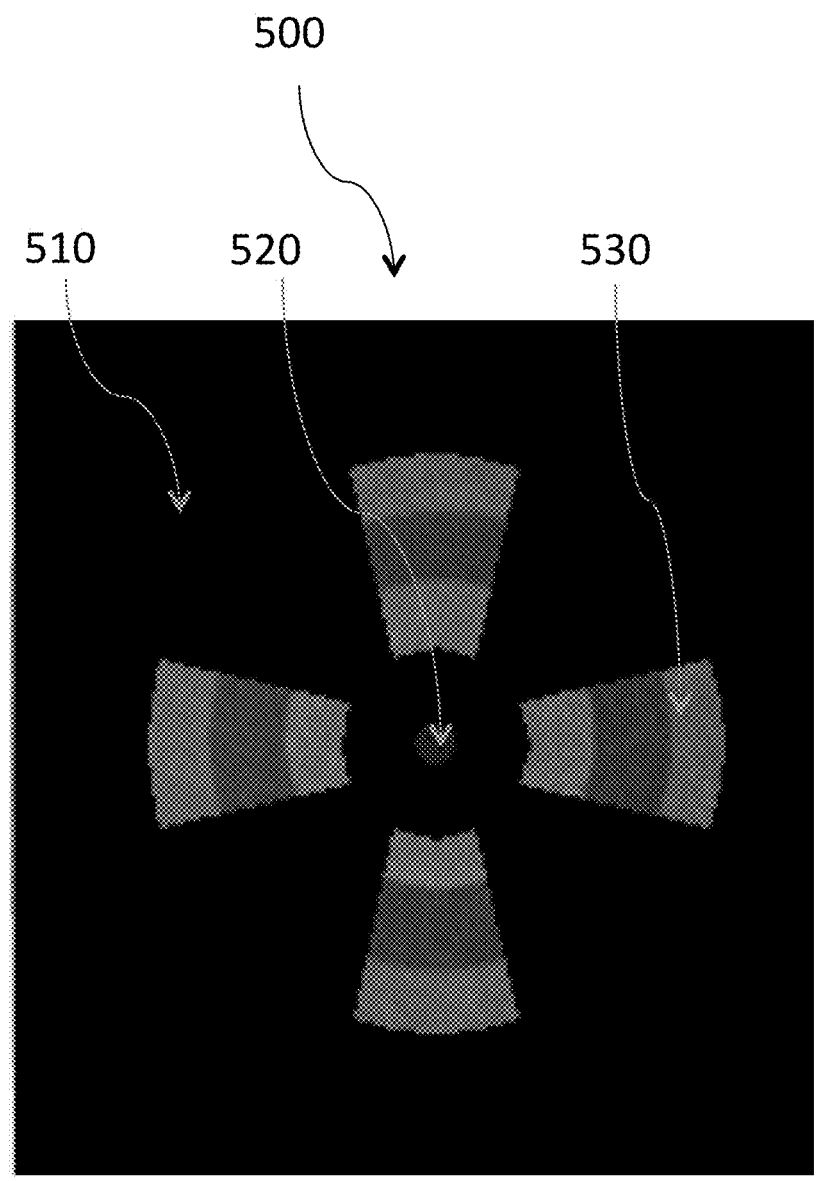
FIG. 6 illustrates a disk with a center hole and auxiliary view ports displaced from the center of a colored bulls eye pattern on a display according to certain embodiments.

In certain embodiments as shown in FIGS. 5 and 6, the movable disks 510 may include one or more view ports 530 through which a user may view a pattern or patterns 200 projected on a display 110. In certain embodiments, the discs 510 may have a central hole 520 and one or more additional view ports 530 to assist the user in aligning the central hole 520 with the center of a pattern projected on the display. The addition of view ports 530 to disks 510 may assist the user in determining the direct to move disks 510 to align center holes 520 with the center 220 of stereo color bulls eye 200. For example, if the center hole 520 is located to the right of the center 220 of stereo color bulls eye 200, view ports 530 may provide the user with an additional visual reference that the disk 510 must be moved to user's left to align with the center 220 of stereo color bulls eye 200 as shown in FIG. 6. Once the disks are properly aligned to permit the eyes to view the center 220 of stereo color bulls eye 200, the IPD can be measured as shown above.

Figure 7:
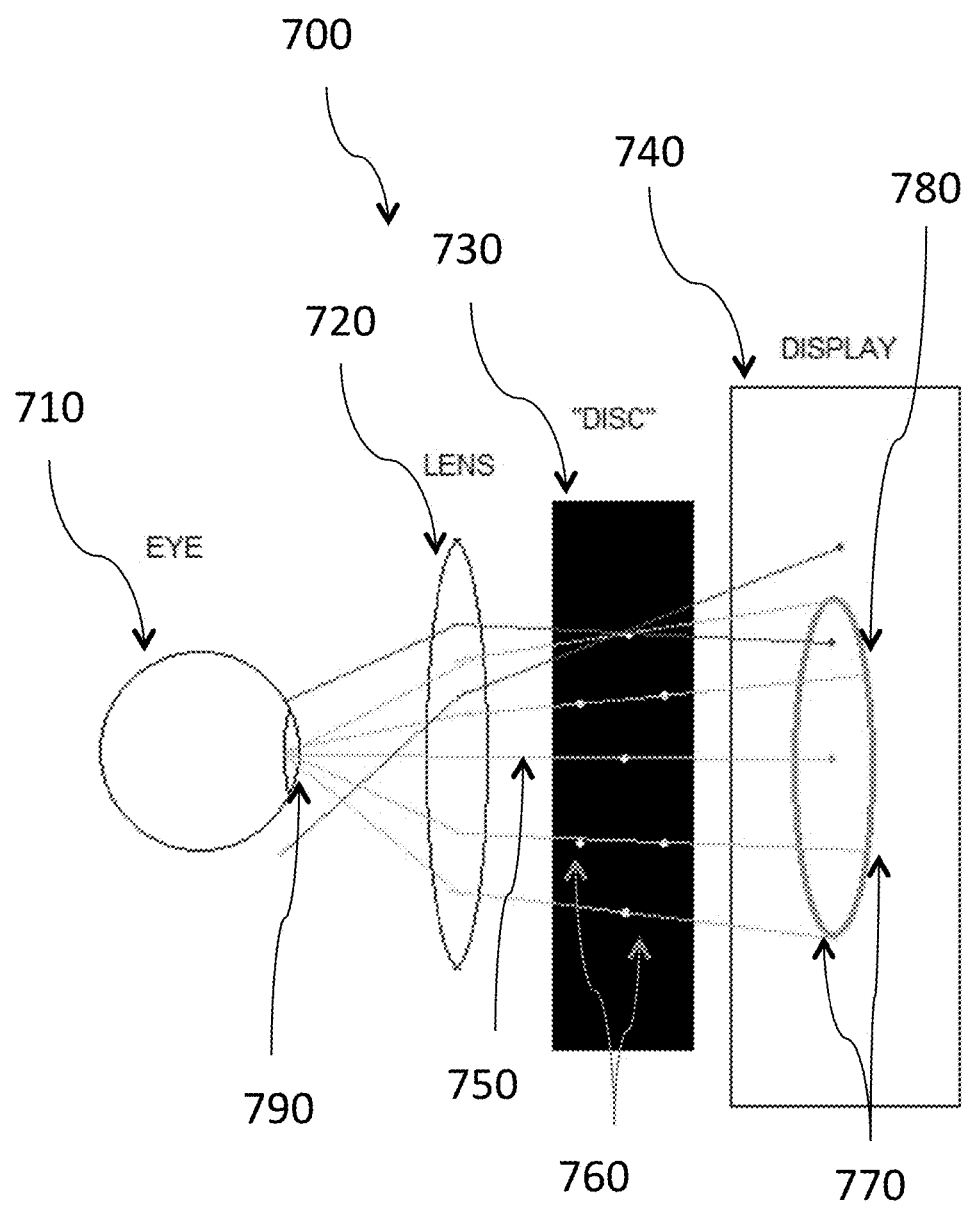
FIG. 7 illustrates a disk with a center hole and auxiliary view ports aligned with the center of a colored bulls eye pattern on a display according to certain embodiments.

As shown in FIG. 7, a head-mounted display system 700 may include one or more lenses 720, one or more discs 730 and one or more displays 740. Certain embodiments may be used to orient the eye 710 into the desired location with respect to the HMD 700. Each lens 720 may have an optical center axis 750 and certain embodiments may assist the user in adjusting the HMD so that their eye 710 is right on this axis 750. As a byproduct of making the adjustments so the user sees the center of the bulls eye to determine the IPD, the user may also be directed to position the eye 710 over the sweet spot on the lens as performance of the HMD 700 degrades if the eye 710 is out of position. Without knowledge of the user's IPD adjustment and/or if the eyes are way out of position on the lens 720, the consequences may not just be that the eyes 710 are in the less than optimal location with respect to the lens 720, but also that any distortion correction calculations that may be done in software assume the eye 710 is on this optimal axis 750. If it's not, then the predistorted image may pass through the wrong parts of the lens such that the image will not be corrected as desired and the original distortion may even be worsened.

In certain embodiments, once the eye 710 is on the optical axis, a further step may be taken to improve understanding of where the eye is and determine how much eye relief is between the eye 710 and the lens 720. This may be very useful in order to know the user's field of view and to refine the distortion correction calculations, which may vary noticeably among users. In certain embodiments, if the user can see through the center hole in the disc and see the center 220 of stereo color bulls eye 200, then you know the eye is on the proper optical axis and looking through the optimal location on the lens. If there are other perforations 760 in the disc, such as holes on a circle around the center, the path from the eye 710 through these holes 760 will land on very specific locations 770 on the display. Pixels on the display 740 that are on the path (green lines) are visible and not on this path are not visible (red lines). For example, in certain embodiments a circle 780 can be drawn on a black background and then the radius of the circle 780 can be changed until the user can see illuminated pixels coming from the circle 780. With knowledge of the radius of the circle 780 and the geometry of the disc 730 and dimensions of the lens 720 and relationship of all the components, the distance between the pupil 790 and eye 710 and the lens 720 that would be able to see light from a circle 780 of that radius.

In certain embodiments, in order to get precise information, some of the dimensions may be small. In certain embodiments, a single pixel, which is on the order of 50 microns, may be illuminated and the holes might be similarly sized. In certain embodiments, measurement to plus-or-minus about 1 mm may be sufficient but because the pupil is large relative to the geometries of the HMD, to get precise measurements other things may need to be tiny.

Certain figures in this specification are flow charts illustrating methods and systems. It will be understood that each block of these flow charts, and combinations of blocks in these flow charts, may be implemented by computer program instructions. These computer program instructions may be loaded onto a computer or other programmable apparatus to produce a machine, such that the instructions which execute on the computer or other programmable apparatus create structures for implementing the functions specified in the flow chart block or blocks. These computer program instructions may also be stored in a computer-readable memory that can direct a computer or other programmable apparatus to function in a particular manner, such that the instructions stored in the computer-readable memory produce an article of manufacture including instruction structures which implement the function specified in the flow chart block or blocks. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flow chart block or blocks.

Accordingly, blocks of the flow charts support combinations of structures for performing the specified functions and combinations of steps for performing the specified functions. It will also be understood that each block of the flow charts, and combinations of blocks in the flow charts, can be implemented by special purpose hardware-based computer systems which perform the specified functions or steps, or combinations of special purpose hardware and computer instructions.

Figure 8:
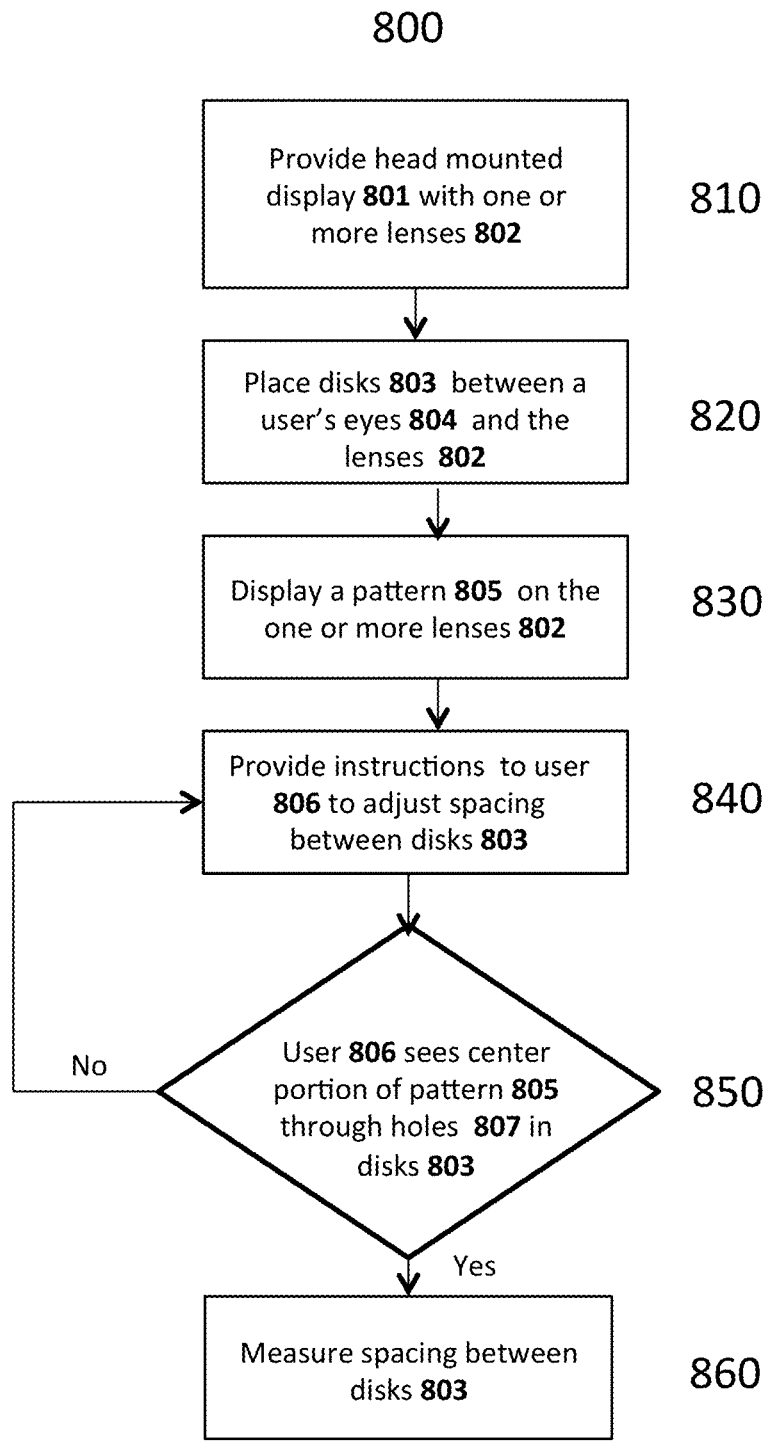
FIG. 8 depicts a flow chart for measuring interpupillary distance according to certain embodiments.

FIG. 8 shows a method 800 of measuring IPD in accordance with certain embodiments. In step 810, a head-mounted display 801 with one or more lenses 802 may be provided. In step 820, a user 806 may place disks 803 between user's eyes 804 and lenses 802. In step 830, a pattern 805 may be displayed on the one or more lenses 802. In step 840, instructions may be provided to user 806 to adjust spacing between disks 803. In step 850, it is determined whether or not the user 806 sees the center portion of pattern 805 through holes 807 in disks 803. If not, step 840 is repeated to provide additional instructions to user 806 to adjust spacing between disks 803. If so, at step 860 the spacing between disks 803 is measured.

For example, any number of computer programming languages, such as C, C++, C# (CSharp), Perl, Ada, Python, Pascal, SmallTalk, FORTRAN, assembly language, and the like, may be used to implement certain embodiments. Further, various programming approaches such as procedural, object-oriented or artificial intelligence techniques may be employed, depending on the requirements of each particular implementation. Compiler programs and/or virtual machine programs executed by computer systems may translate higher level programming languages to generate sets of machine instructions that may be executed by one or more processors to perform a programmed function or set of functions.

The term "machine-readable medium" should be understood to include any structure that participates in providing data which may be read by an element of a computer system. Such a medium may take many forms, including but not limited to, non-volatile media, volatile media, and transmission media. Non-volatile media include, for example, optical or magnetic disks and other persistent memory. Volatile media include dynamic random access memory (DRAM) and/or static random access memory (SRAM). Transmission media include cables, wires, and fibers, including the wires that comprise a system bus coupled to processor. Common forms of machine-readable media include, for example, a floppy disk, a flexible disk, a hard disk, a magnetic tape, any other magnetic medium, a CD-ROM, a DVD, any other optical medium.

Figure 9A:
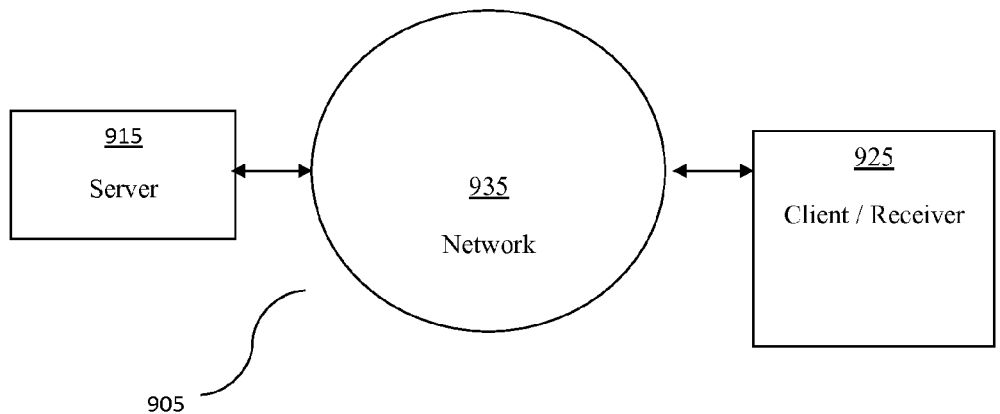
FIG. 9A illustrates an exemplary networked environment and its relevant components according to certain embodiments.

FIG. 9A depicts an exemplary networked environment 905 in which systems and methods, consistent with exemplary embodiments, may be implemented. As illustrated, networked environment 905 may include a server 915, a client/receiver 925, and a network 935. The exemplary simplified number of servers 915, clients/receivers 925, and networks 935 illustrated in FIG. 9A can be modified as appropriate in a particular implementation. In practice, there may be additional servers 915, clients/receivers 925, and/or networks 935.

Network 935 may include one or more networks of any type, including a Public Land Mobile Network (PLMN), a telephone network (e.g., a Public Switched Telephone Network (PSTN) and/or a wireless network), a local area network (LAN), a metropolitan area network (MAN), a wide area network (WAN), an Internet Protocol Multimedia Subsystem (IMS) network, a private network, the Internet, an intranet, and/or another type of suitable network, depending on the requirements of each particular implementation.

One or more components of networked environment 905 may perform one or more of the tasks described as being performed by one or more other components of networked environment 905.

Figure 9B:
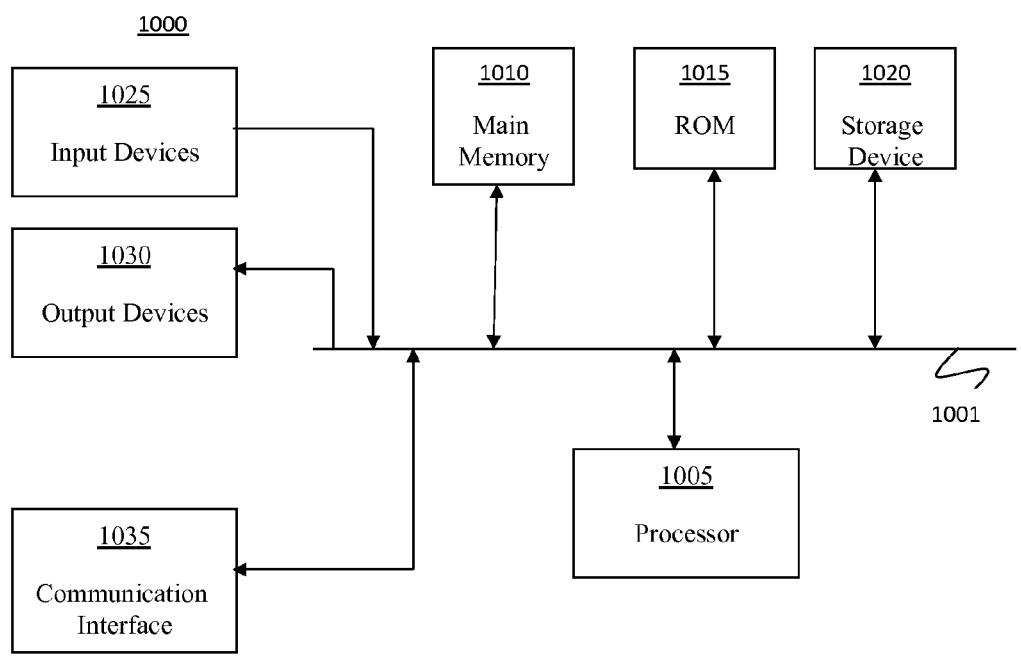
FIG. 9B is an exemplary block diagram of a computing device that may be used to implement certain embodiments.

FIG. 9B is an exemplary diagram of a computing device 1000 that may be used to implement certain embodiments, such as aspects of server 915 or of client/receiver 925. Computing device 1000 may include a bus 1001, one or more processors 1005, a main memory 1010, a read-only memory (ROM) 1015, a storage device 1020, one or more input devices 1025, one or more output devices 1030, and a communication interface 1035. Bus 1001 may include one or more conductors that permit communication among the components of computing device 1000.

Processor 1005 may include any type of conventional processor, microprocessor, or processing logic that interprets and executes instructions. Main memory 1010 may include a random-access memory (RAM) or another type of dynamic storage device that stores information and instructions for execution by processor 1005. ROM 1015 may include a conventional ROM device or another type of static storage device that stores static information and instructions for use by processor 1005. Storage device 1020 may include a magnetic and/or optical recording medium and its corresponding drive.

Input device(s) 1025 may include one or more conventional mechanisms that permit a user to input information to computing device 1000, such as a keyboard, a mouse, a pen, a stylus, handwriting recognition, voice recognition, biometric mechanisms, and the like. Output device(s) 1030 may include one or more conventional mechanisms that output information to the user, including a display, a projector, an A/V receiver, a printer, a speaker, and the like. Communication interface 1035 may include any transceiver-like mechanism that enables computing device/server 1000 to communicate with other devices and/or systems. For example, communication interface 1035 may include mechanisms for communicating with another device or system via a network, such as network 1035 as shown in FIG. 3A.

As will be described in detail below, computing device 1000 may perform operations based on software instructions that may be read into memory 1010 from another computer-readable medium, such as data storage device 1020, or from another device via communication interface 1035. The software instructions contained in memory 1010 cause processor 1005 to perform processes that will be described later. Alternatively, hardwired circuitry may be used in place of or in combination with software instructions to implement processes consistent with the present invention. Thus, various implementations are not limited to any specific combination of hardware circuitry and software.

Certain embodiments of the present invention described herein are discussed in the context of the global data communication network commonly referred to as the Internet. Those skilled in the art will realize that embodiments of the present invention may use any other suitable data communication network, including without limitation direct point-to-point data communication systems, dial-up networks, personal or corporate Intranets, proprietary networks, or combinations of any of these with or without connections to the Internet.

While the above description contains many specifics and certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those ordinarily skilled in the art, as mentioned above. The invention includes any combination or subcombination of the elements from the different species and/or embodiments disclosed herein.

We claim:

1. A device for measuring interpupillary distance in a head-mounted display, comprising:
   one or more display lenses for displaying one or more patterns;
   a first movable disk for placement between a left eye of a user and at least one of the one or more display lenses, the first movable disk comprising a first hole;
   a second movable disk for placement between a right eye of the user and at least one of the one or more display lenses, the second movable disk comprising a second hole;
   a processor for providing instructions to a user to adjust the position of the first movable disk and the second movable disk until the user can see only a center portion of the one or more patterns through the first movable disk and the second movable disk; and
   a measurement device for measuring the distance between the first movable disk and the second movable disk.

2. The device of claim 1, wherein the first movable disk is configured to be removed from between the left eye and the one or more displays and the second movable disk is configured to be removed from between the right eye and the one or more displays.

3. The device of claim 1, wherein the measurement device comprises at least one of a linear potentiometer, a rotary potentiometer with a connecting rod, a hall-effect sensor with one or more magnets, a linear variable differential transformer, an optical sensor with a code-strip, and an elastomeric potentiometer.

4. The device of claim 1, wherein the first hole and the second hole are configured to limit a user's vision to be on-axis with respect to the one or more display lenses.

5. The device of claim 1, wherein the one or more patterns comprises a stereo colored bulls eye pattern.

6. The device of claim 5, wherein the center portion of the one or more patterns comprises a color.

7. The device of claim 1, wherein the one or more patterns comprises a first pattern comprising a plurality of vertical stripes, a second pattern comprising a plurality of horizontal stripes and a third pattern comprising stereo colored bulls eye pattern and wherein the processor is configured to provide instructions to a user to adjust the position of the first movable disk and the second movable disk until the user can see only a center portion of the each of one or more patterns through the first movable disk and the second movable disk.

8. The device of claim 7, wherein the center portion of the first pattern comprises a first color, the center portion of the second pattern comprises a second color, and the center portion of the third pattern comprises a third color.

* * * * *